US00PP19858P2

(12) United States Plant Patent
Glenn

(10) Patent No.: US PP19,858 P2
(45) Date of Patent: Mar. 24, 2009

(54) OAK TREE NAMED 'QNSTG'

(50) Latin Name: *Quercus nuttalli*
Varietal Denomination: QNSTG

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 11/639,127

(22) Filed: Dec. 13, 2006

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

| | | | |
|---|---|---|---|
| PP4,149 | P | 11/1977 | Schmidt, III |
| PP13,524 | P3 | 1/2003 | Strickland |
| PP14,424 | P3 | 12/2003 | Strickland |
| PP16,254 | P3 | 2/2006 | Glenn |
| PP16,401 | P3 | 4/2006 | Glenn |

OTHER PUBLICATIONS

U.S. Appl. No. 11/638,930, filed Dec. 13, 2006, Glenn.

*Primary Examiner*—Annette H Para
(74) *Attorney, Agent, or Firm*—Klarquist Sparkman, LLP

(57) ABSTRACT

An Oak tree named 'QNSTG' having an upright branching habit and consistent red new growth persisting in summer, and also capable of being reproduced reliably using vegetative cuttings.

7 Drawing Sheets

Latin name of genus and species: *Quercus* sp.
Variety denomination: 'QNSTG'.

BACKGROUND OF THE INVENTION

The present invention relates to a new and distinct variety of *Quercus* sp., which has been given the varietal name 'QNSTG'. I discovered my new tree in 1996 in a cultivated area of a nursery in Oconee County, Georgia.

The parentage of this tree is unclear. It is definitely a red oak type tree. Representative species include Pin Oak, *Q. palustris,* palustris or Red Oak, *Q. rubra.* rubra. There are also several related species, including Nuttall Oak (*Q. nuttallii*), Shumard Oak (*Q. shumardii*), and Scarlet Oak (*Q. coccinea*). My new tree has characteristics and a history that have prevented making an exact identification of its species, but Nuttall Oak appears to be the closest.

Nuttall Oak, as well as most other red oak types, readily hybridize with one another, and there is a high probability that this tree is a result of a cross between a Nuttall Oak and Shumard Oak or some other species of red oak, since Nuttall Oak and Shumard Oak overlap one another across much of their range. For example, in Texas, Nuttall is found in the lower Southeast corner of the state, Shumard is located in a wide band covering most of the eastern part of the state, and Texas Red Oak, *Q. texana* is the primary tree in the central part of the state east of Dallas. There is also a large swath of habitat between the primary Shumard and Texas Red Oak regions where the predominant tree is a hybrid between Shumard and Texas Red Oak. Hybrids are common and can easily make up a large population of the trees in any given area.

My original tree had been purchased as a 12 to 18 inch liner in spring 1995 and at that time planted in a cultivated nursery field. Then the original tree, a seedling, was moved to a nursery in Bulloch County, Georgia. in spring 1998. In January 2002, it was transplanted to an observation area where it has remained since that time. It is now 11 years old from a seed. The description of this new Oak variety is based on observations of this original tree and of asexually propagated progeny, asexually propagated in Bulloch County, Georgia and in Oconee County, Georgia, produced from vegetative propagation. These asexually propagated progeny are being grown at a nursery in Oconee County, Georgia and at a nursery in Bulloch County, Georgi.

The original tree has displayed characteristics resembling Nuttall Oak and Shumard Oak. There is much confusion over the exact identification of this tree, and several experienced individuals have expressed differing opinions. The only consistency has been the opinion that the acorn is generally the most distinguishing characteristic determining the species difference between Nuttall Oak and Shumard Oak. When compared to the above oaks, the acorns on my new tree most resemble Nuttall Oak, which indicates that the tree is most likely a Nuttall Oak or at least has Nuttall Oak as one of its parents. Other physical characteristics of the tree, such as leaf size, sinus depth, or bud features, do not provide definitive answers as to the true parentage of the tree.

BRIEF SUMMARY OF THE INVENTION

As I observed the original tree of my new variety, the uniqueness of this tree became apparent because of its upright branching habit and consistent red new growth persisting into summer. These characteristics distinguish my new tree from other Nuttall Oaks of which I am aware.

In 2001, progeny from my original tree was successfully propagated by vegetative cuttings at my direction, and the progeny have thus far proven to retain the upright branching habit and consistent red new growth persisting into summer of the original tree, even as smaller plants.

I observed this tree of my new variety for a period of time and believe it is particularly useful as a specimen or for groupings in lawns, parks, golf courses, commercial landscapes, and as a street tree. It provides good shade, has an above average growing rate, and has good structural branching. It also provides ornamental interest with its consistent red new growth persisting in summer.

Cultivated Nuttall Oak is represented in the industry mostly by seedling material. Seedling material has a wide range of variability, and as is illustrated by information in this patent, there may be uncertainty as to the trueness of type from the seed. My new tree has an upright branching habit and consistent red new growth (like RHS 46A) persisting in summer not represented consistently by any other Nuttall Oak tree cultivar known to me. 'QNFTA' (U.S. Plant Pat. No. 13,524) and 'QNSTC' (U.S. Plant Pat. No. 16,401) are Nuttall cultivars that have an upright-pyramidal branching habit, and a consistent red fall colored foliage. However, both of these selections lack a consistent red new growth persisting into summer. 'QNSTD' (U.S. Plant Pat. No. 16,254) is a Nuttall Oak cultivar with new deep red foliage growth (like RHS 59A) persisting into summer; however, it differs from my new tree by being darker red in color.

Typical Nuttall and Shumard are pyramidal trees that become more spreading with age. My tree has a dense shape. My new tree has a full, dense canopy and a central leader that is more typical of a Nuttall Oak tree. Both Nuttall Oak and Shumard Oak typically reach 40 to 60 feet high and wide in the landscape, but can reach 100 feet or more in nature. The ultimate height and width of my new variety is not known.

My new variety has been asexually propagated at my direction at a nursery in Oconee County, Georgia by softwood cuttings. Asexual propagation was accomplished in Oconee County, Georiga. This propagation and observation of the resulting progeny have proven the characteristics of my new variety to be firmly fixed and to reproduce true to type. Furthermore, these observations have confirmed that my new variety represents a new and improved variety of oak tree, which appears to be a variation of Nuttall Oak trees based upon observations of acorns in the original tree and as particularly evidenced by the upright branching pattern and consistent red new growth persisting in summer, and which can reliably be asexually propagated using vegetative propagation.

BRIEF DESCRIPTION OF THE DRAWINGS

The accompanying photographs depict the color of the tree and foliage of my new variety as nearly as is reasonably possible to make the same in a color illustration of this character.

DETAILED BOTANICAL DESCRIPTION

My 'QNSTG' variety of Oak tree is currently growing at an observation site in Oconee County, Georgia. It is located in an are a of Oconee that has a clay loam soil type and receives approximately 50 inches of rain per year. Oconee County, Georgia in USDA Hardiness Zone 7. Both Nuttall and Shumard are typically hardy in USDA Zones 5 through 9.

My new tree has not been observed under all growing conditions, and thus, variations may occur as a result of different growing conditions. The following is a detailed description of my new variety of my new tree with color terminology in accordance with the Royal Horticultural Society (R.H.S.) Colour Chart published by the Royal Horticultural Society in London. The observations are of the original tree growing at the observation site in Oconee County, Georgia.

Parentage: Selected as a seedling growing in a cultivated field at a nursery in Oconee County, Georgia. The parentage of this tree is believed to include Nuttall Oak, but is not extremely clear for reasons explained above.

Figure 1:
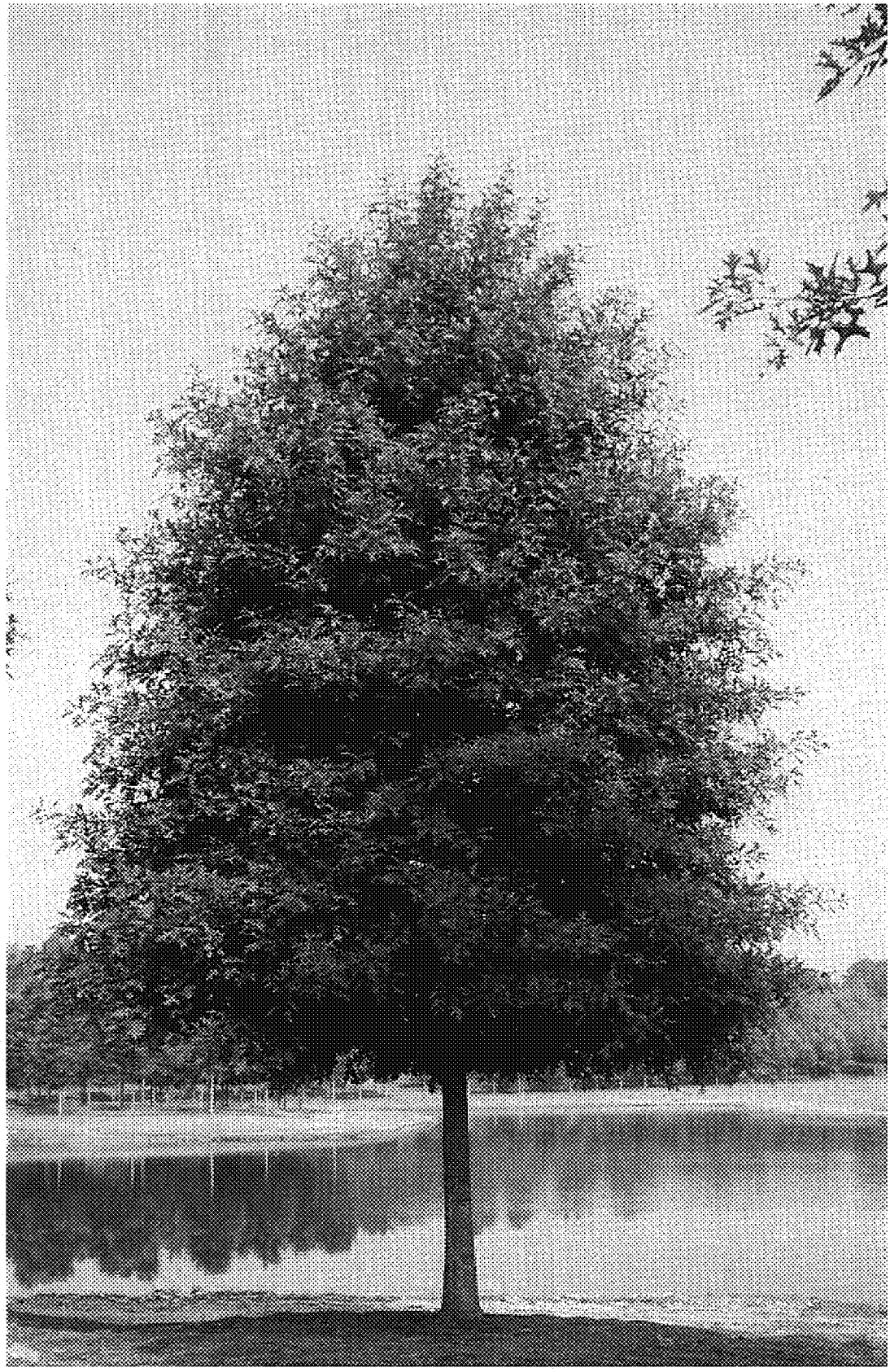
FIG. 1 is a photograph of the original tree of my new variety in summer leaf.
Figure 2:
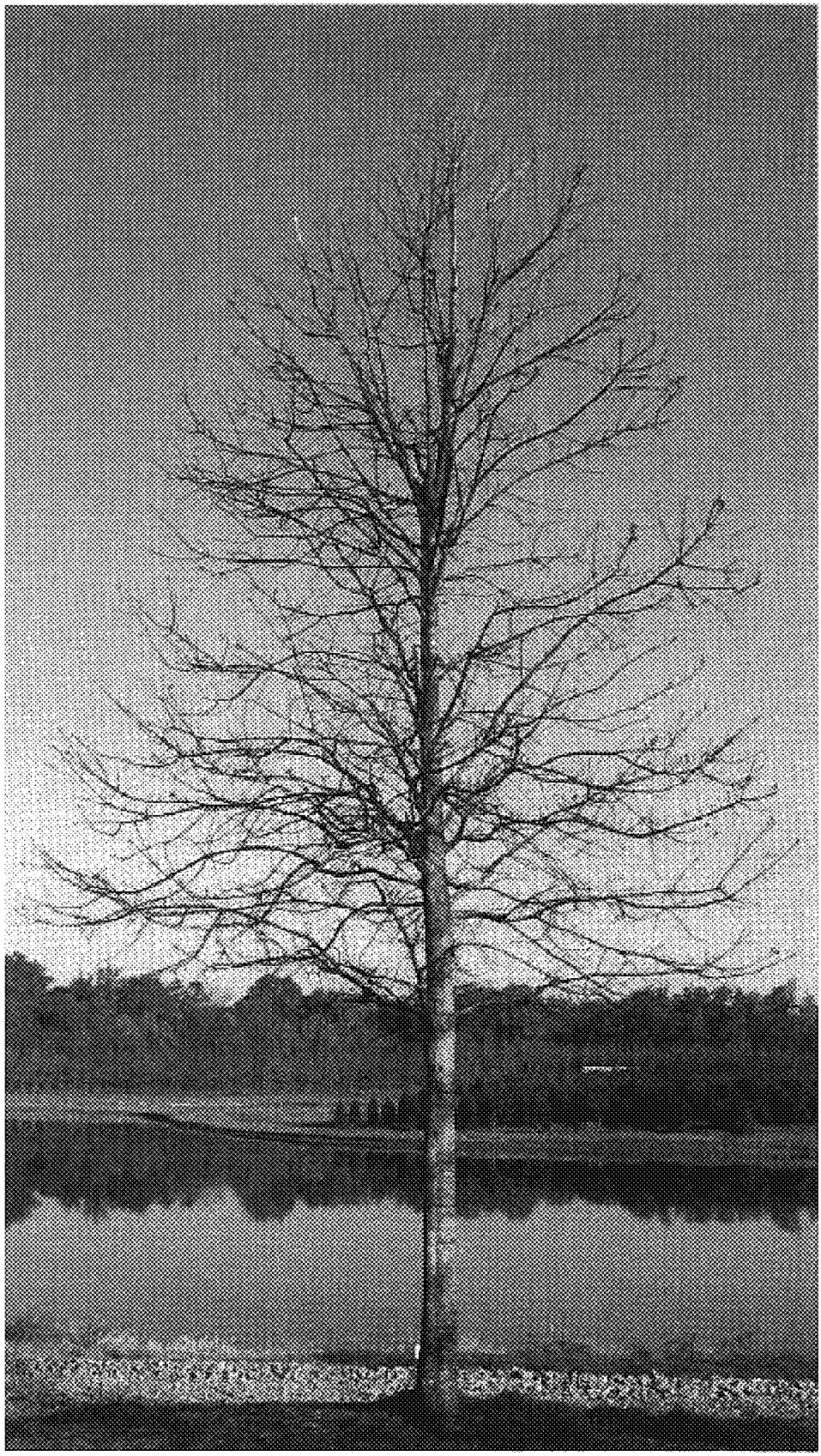
FIG. 2 is a photograph of the original tree of the new variety during winter season.
Figure 3:
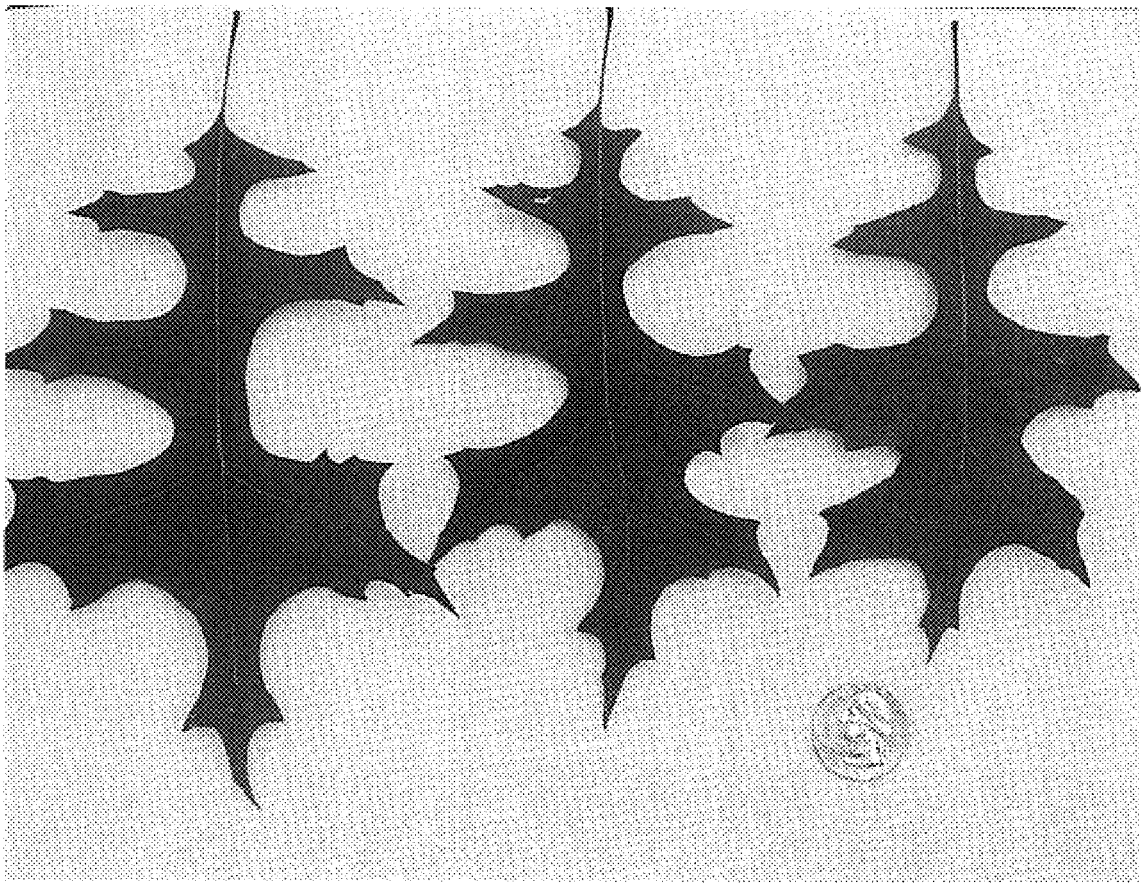
FIG. 3 is a close up of the upper side of three single leaves depicting the upper side of leaves from a tree of my new variety. The US Quarter Dollar in the picture provides a sizing reference.

Tree Shape: The original tree has a dense canopy, with a central leader (FIGS. 1 and 2).

Size and growth rate: The original tree is currently 9 inches in caliper at 12 inches above the ground, about 27 feet high, and about 18 feet wide, thus providing an overall height to width ration of about 1.5. Prior to transplanting to the observation site, the original tree had an average growth in caliper of about 1.2 inches per year. Root development from time of sticking vegetative cuttings is approximately six to eight weeks.

Figure 7:
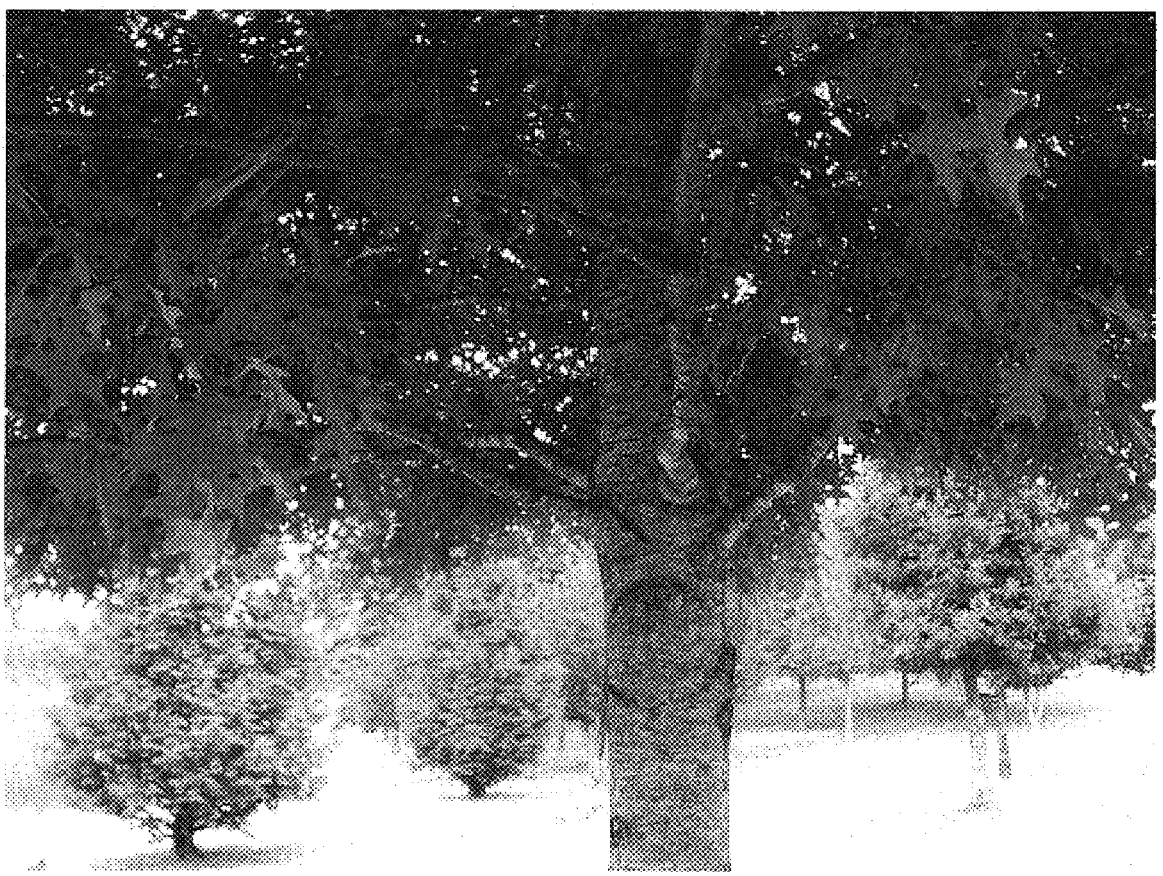
FIG. 7 is a close up of the branching habit of the new variety.

Trunk: Bark is typical of the species (FIG. 7), being smooth and gray (grayed-green) (RHS 198A) with patches of light gray (RHS 198D) on young trees, with age, becoming roughened by shallow ridges and furrows. Mature bark is darker gray (RHS 202B) with patches of light gray (RHS 198D) in color, also typical of the species. Lenticels are vertical in orientation. They average approximately three to four inches long and one-fourth to one-third inches wide. Lenticels are gray-orange (RHS 164A).

Branching habit: Primary branches emerge from the trunk at about a 45 degree angle to the leader. Some of the branches in the top one-half of the tree emerge at slightly less of an angle, approx. 35 degree angle to the leader. We expect with age the angle to increase with respect to the leader.

Figure 4:
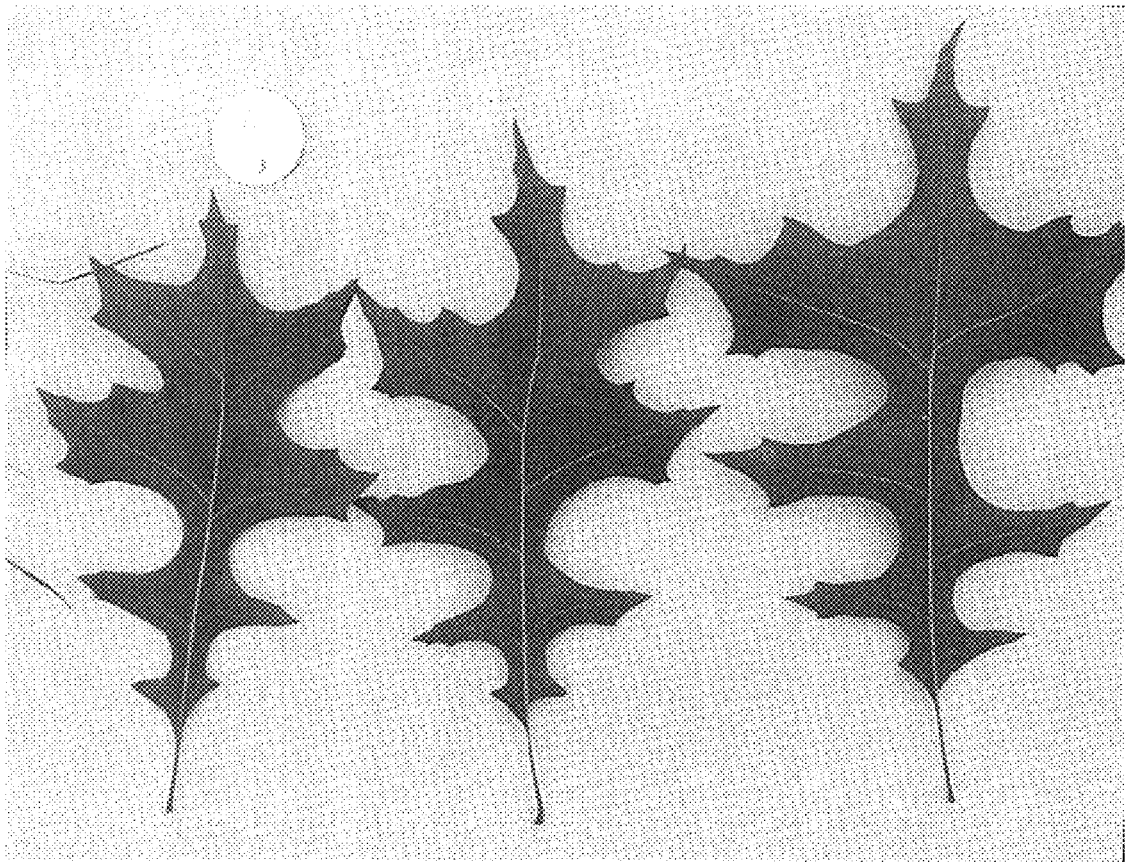
FIG. 4 is a close up of the underside of three single leaves from the tree of my new variety.
Figure 5:
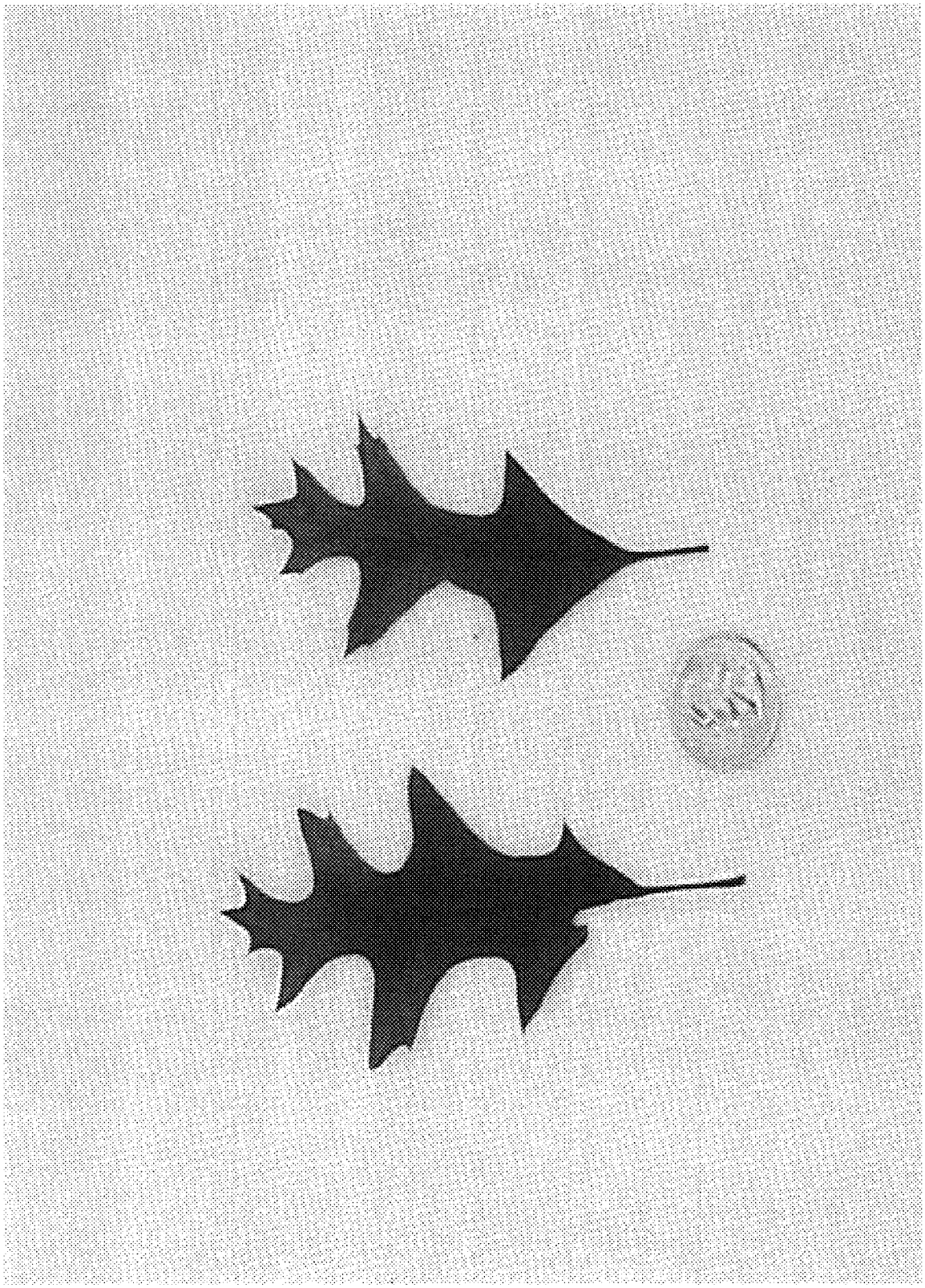
FIG. 5 is a close up of two leaves depicting the new growth color during the spring.
Figure 6:
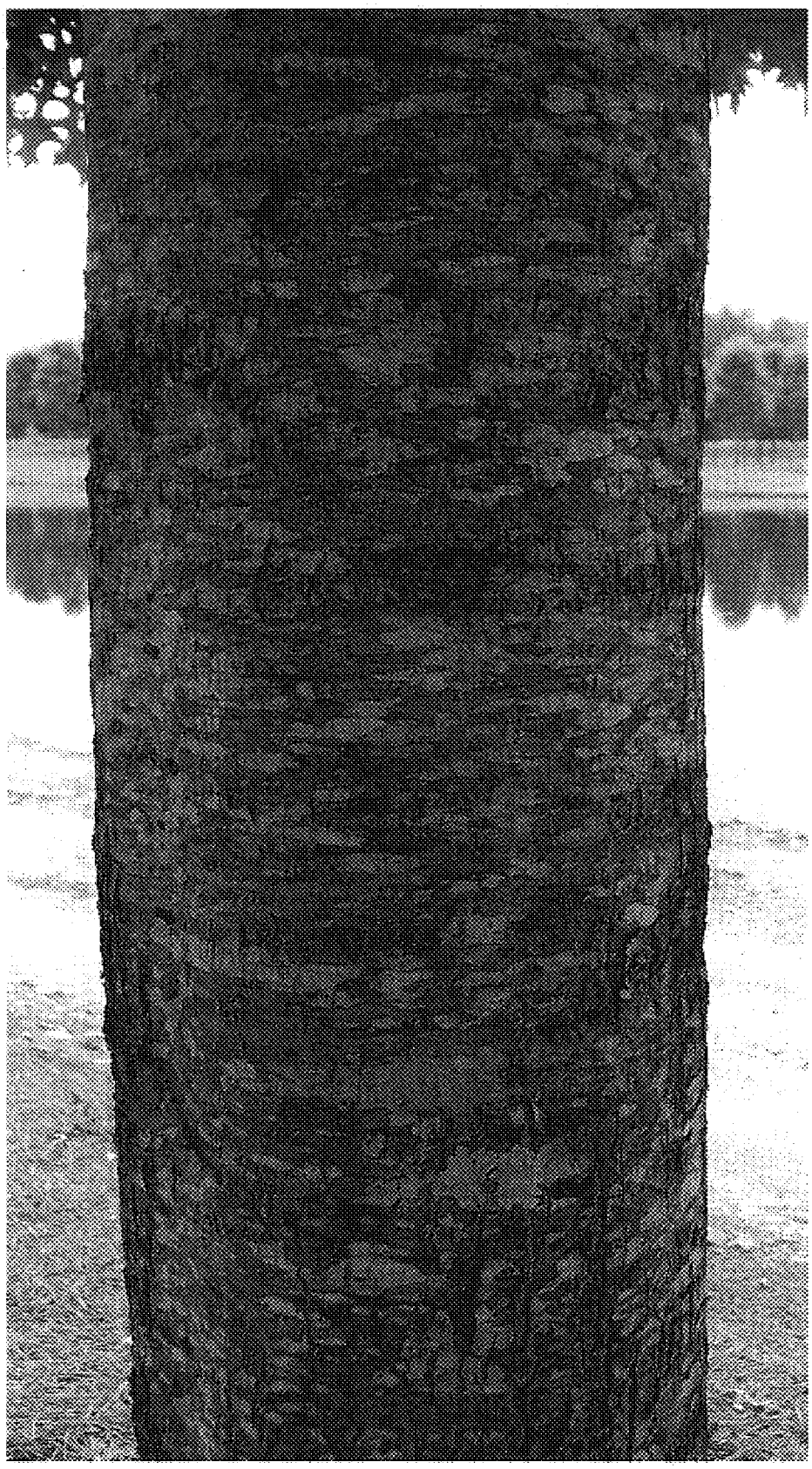
FIG. 6 is a close up of a typical section of the trunk of the original tree of the new variety.

Foliage: The leaves of Nuttall, Shumard, and Pin all resemble one another, and my tree has leaves that are typical of the species *Q. nuttallii* in size and shape: Alternate, simple, obovate to elliptic, 4 to 9" long, 2 to 5" wide, with 5 to 9 lobes. Sinuses are round with narrow lobes. The leaves maintain a dark green color in summer (FIG. 4) (RHS 137A), and the lower leaf surface (FIG. 5) is a lighter green (RHS 137B). My new tree has consistent fall color which ranges from orange-red to yellow-orange. New growth in the spring (FIG. 2 and 6) is a consistent deep red (RHS 46A) and persists into summer. The stems turn a deep red (RHS 59A) in the spring during leaf out before turning back to the normal pigmentation. The petioles average approximately 0.9 inch in length. The petioles are yellow-green in color (RHS 146B). with some grey-red (RHS 184A) at the base.

Buds: Typical of the species, being imbricate, ⅛ to ¼" long, ash-gray to brown-gray, and pubescent with ciliate scale margins.

Flowers: Typical of the species. However, most oaks have flowers so similar that it is difficult to distinguish between species based on flower type alone. The trees are monoecious. The staminate catkins are pendent and clustered. The individual flowers comprise a 4- to 7-lobed calyx that encloses 6 to 12 stamens. Pistillate flowers are solitary or in few to many-flowered spikes from the axils of the new leaves. Individual pistillate flowers consist of a 6-lobed calyx surrounding the ovary, with the whole partly enclosed in an involucre.

Fruit: Acorns are typical of species. Acorns are ovate, ¾ to 1¼" long, short-stalked, oblong-ovoid, and covered ⅓ to ½ by the cap. The acorn is gray-orange (RHS 165A) in color with dark brown striations (RHS 200B). The cap is light brown (RHS 199C).

Root System: The root system is typical of the species being fibrous.

Winter Hardiness: Observed to be hardy in at least USDA Hardiness Zone 7. My new tree variety has not been observed under multiple Zones.

Disease and pest resistance: My new tree variety appears to be typical of the species.

I claim:

1. A new and distinct variety of Oak tree substantially as herein shown and described, characterized particularly as to novelty by its upright branching habit and its consistent red new growth persisting into summer.

* * * * *

UNITED STATES PATENT AND TRADEMARK OFFICE

CERTIFICATE OF CORRECTION

PATENT NO. : PP19,858 P2
APPLICATION NO. : 11/639127
DATED : March 24, 2009
INVENTOR(S) : Michael Glenn It is certified that error appears in the above-identified patent and that said Letters Patent is hereby corrected as shown below:

In the Specification:

Column 1, lines 11-12, "Representative species include Pin Oak, *Q. palustris*, palustris or Red Oak, *Q. rubra*, rubra.", should read --Representative species include Pin Oak, *Q. palustris*, or Red Oak, *Q. rubra.*--

Column 1, line 36, "Georgia, in spring 1998.", should read --Georgia in spring 1998.--

Column 2, line 9, "Georgi.", should read --Georgia.--

Column 3, line 35, "Georiga.", should read --Georgia.--

Column 4, line 10, "are a", should read --area--

Column 4, line 12, "in USDA", should read --is in USDA--

Column 5, line 12, "(RHS 146B). with", should read --(RHS 146B), with--

Signed and Sealed this
Fourteenth Day of August, 2012

David J. Kappos

David J. Kappos
*Director of the United States Patent and Trademark Office*